United States Patent
Frasier

(10) Patent No.: US 8,876,905 B2
(45) Date of Patent: Nov. 4, 2014

(54) MINIMALLY INVASIVE CORPECTOMY CAGE AND INSTRUMENT

(75) Inventor: William Frasier, New Bedford, MA (US)

(73) Assignee: DePuy Synthes Products, LLC, Ranham, MA (US)

( * ) Notice: Subject to any disclaimer, the term of this patent is extended or adjusted under 35 U.S.C. 154(b) by 940 days.

(21) Appl. No.: 12/432,117

(22) Filed: Apr. 29, 2009

(65) Prior Publication Data

US 2010/0280616 A1    Nov. 4, 2010

(51) Int. Cl.
*A61F 2/44*      (2006.01)
*A61F 2/46*      (2006.01)
*A61F 2/30*      (2006.01)

(52) U.S. Cl.
CPC ......... *A61F 2/44* (2013.01); *A61F 2002/30242* (2013.01); *A61F 2002/30601* (2013.01); *A61F 2002/30787* (2013.01); *A61F 2002/30507* (2013.01); *A61F 2002/4475* (2013.01); *A61F 2250/0006* (2013.01); *A61F 2/4611* (2013.01); *A61F 2220/0025* (2013.01); *A61F 2002/30551* (2013.01); *A61F 2230/0071* (2013.01); *A61F 2002/30841* (2013.01); *A61F 2002/30495* (2013.01); *A61F 2002/30522* (2013.01); *A61F 2002/30538* (2013.01)
USPC ..................................... 623/17.16; 623/17.11

(58) Field of Classification Search
USPC .......... 623/17.11–17.16; 606/246–279, 86 A, 606/105
See application file for complete search history.

(56) References Cited

U.S. PATENT DOCUMENTS

| 4,657,550 A | 4/1987 | Daher |
| 4,911,718 A | 3/1990 | Lee |
| 4,961,740 A | 10/1990 | Ray |
| 5,026,373 A | 6/1991 | Ray |
| 5,122,130 A | 6/1992 | Keller |
| 5,171,281 A | 12/1992 | Parsons |
| 5,236,460 A | 8/1993 | Barber |
| 5,290,312 A | 3/1994 | Kojimoto |
| 5,458,641 A | 10/1995 | Ramirez Jimenez |
| 5,510,370 A | 4/1996 | Hock |

(Continued)

FOREIGN PATENT DOCUMENTS

| DE | 3023942 | 1/1982 |
| DE | 20004812 | 11/2000 |

(Continued)

OTHER PUBLICATIONS

Russegger, "First Experiences With a Distractible Titanium Implant in Vvntral Cervical Disc Surgery: Report on 30 Consecutive Cases", *Eur Spine J*, 1997; 6(1), pp. 91-97.

(Continued)

*Primary Examiner* — Jerry Cumberledge
*Assistant Examiner* — Nicholas Plionis

(57) ABSTRACT

An assembly comprising an expandable corpectomy cage and an insertion instrument, wherein the expandable cage comprises an instrument attachment features, including mating holes on the sides of the outer sleeve, and a ball-shaped pocket on the endplate of the inner sleeve, and the insertion instrument features a tuning-fork shaped holder, which attaches to the mating holes on the implant's outer sleeve using small bosses which mate with the holes under the spring tension of the fork, and a lever with a spherical end that mates with the ball-shaped pocket in the inner sleeve endplate.

3 Claims, 14 Drawing Sheets

(56) References Cited

U.S. PATENT DOCUMENTS

| | | | |
|---|---|---|---|
| 5,545,229 A | 8/1996 | Parsons | |
| 5,571,190 A | 11/1996 | Ulrich | |
| 5,571,192 A | 11/1996 | Schonhoffer | |
| 5,658,335 A | 8/1997 | Allen | |
| 5,683,408 A * | 11/1997 | De Laage De Meux et al. | 606/184 |
| 5,702,451 A | 12/1997 | Biedermann | |
| 5,702,453 A | 12/1997 | Rabbe | |
| 5,702,455 A | 12/1997 | Saggar | |
| 5,723,013 A | 3/1998 | Jeanson | |
| 5,776,197 A | 7/1998 | Rabbe | |
| 5,776,198 A | 7/1998 | Rabbe | |
| 5,827,328 A | 10/1998 | Buttermann | |
| 5,856,138 A | 1/1999 | Fukuda | |
| 5,860,977 A | 1/1999 | Zucherman | |
| 5,876,404 A | 3/1999 | Zucherman | |
| 5,916,267 A | 6/1999 | Tienboon | |
| 5,972,031 A | 10/1999 | Biedermann | |
| 5,989,290 A | 11/1999 | Biedermann | |
| 6,015,436 A | 1/2000 | Schonhoffer | |
| 6,048,342 A | 4/2000 | Zucherman | |
| 6,049,026 A | 4/2000 | Muschler | |
| 6,066,175 A | 5/2000 | Henderson | |
| 6,068,630 A | 5/2000 | Zucherman | |
| 6,074,390 A | 6/2000 | Zucherman | |
| 6,080,193 A | 6/2000 | Hochshuler | |
| 6,086,613 A | 7/2000 | Camino | |
| 6,090,112 A | 7/2000 | Zucherman | |
| 6,126,660 A | 10/2000 | Dietz | |
| 6,149,652 A | 11/2000 | Zucherman | |
| 6,152,926 A | 11/2000 | Zucherman | |
| 6,156,038 A | 12/2000 | Zucherman | |
| 6,174,334 B1 | 1/2001 | Suddaby | |
| 6,176,881 B1 | 1/2001 | Schär | |
| 6,183,471 B1 | 2/2001 | Zucherman | |
| 6,190,387 B1 | 2/2001 | Zucherman | |
| 6,190,413 B1 | 2/2001 | Sutcliffe | |
| 6,193,755 B1 | 2/2001 | Metz-Stavenhagen | |
| 6,193,756 B1 | 2/2001 | Studer | |
| 6,200,348 B1 | 3/2001 | Biedermann | |
| 6,235,030 B1 | 5/2001 | Zucherman | |
| 6,238,397 B1 | 5/2001 | Zucherman | |
| 6,261,296 B1 | 7/2001 | Aebi | |
| 6,280,444 B1 | 8/2001 | Zucherman | |
| 6,296,647 B1 | 10/2001 | Robioneck | |
| 6,299,644 B1 | 10/2001 | Vanderschot | |
| 6,319,257 B1 | 11/2001 | Carignan | |
| 6,332,882 B1 | 12/2001 | Zucherman | |
| 6,332,883 B1 | 12/2001 | Zucherman | |
| 6,332,895 B1 | 12/2001 | Suddaby | |
| 6,344,057 B1 | 2/2002 | Rabbe | |
| 6,352,556 B1 | 3/2002 | Kretschmer | |
| 6,375,681 B1 | 4/2002 | Truscott | |
| 6,379,355 B1 | 4/2002 | Zucherman | |
| 6,419,676 B1 | 7/2002 | Zucherman | |
| 6,419,677 B2 | 7/2002 | Zucherman | |
| 6,419,705 B1 | 7/2002 | Erickson | |
| 6,451,020 B1 | 9/2002 | Zucherman | |
| 6,454,806 B1 | 9/2002 | Cohen | |
| 6,478,796 B2 | 11/2002 | Zucherman | |
| 6,500,178 B2 | 12/2002 | Zucherman | |
| 6,514,256 B2 | 2/2003 | Zucherman | |
| 6,524,341 B2 | 2/2003 | Läng | |
| 6,527,803 B1 | 3/2003 | Crozet | |
| 6,562,074 B2 | 5/2003 | Gerbec | |
| 6,590,081 B1 | 7/2003 | Zhang | |
| 6,616,695 B1 | 9/2003 | Crozet | |
| 6,660,038 B2 | 12/2003 | Boyer, II | |
| 6,712,825 B2 | 3/2004 | Aebi | |
| 6,716,218 B2 | 4/2004 | Holmes | |
| 6,730,088 B2 | 5/2004 | Yeh | |
| 6,752,832 B2 | 6/2004 | Neumann | |
| 6,758,862 B2 | 7/2004 | Berry | |
| 6,776,197 B1 | 8/2004 | DeCrane | |
| 6,776,798 B2 | 8/2004 | Camino | |
| 6,805,714 B2 | 10/2004 | Sutcliffe | |
| 6,808,538 B2 | 10/2004 | Paponneau | |
| 6,830,589 B2 | 12/2004 | Erickson | |
| 6,866,682 B1 | 3/2005 | An | |
| 6,899,734 B2 | 5/2005 | Castro | |
| 6,902,579 B2 | 6/2005 | Harms | |
| 6,908,485 B2 | 6/2005 | Crozet | |
| 6,908,495 B2 | 6/2005 | Northrop | |
| 6,926,728 B2 | 8/2005 | Zucherman | |
| 6,929,662 B1 | 8/2005 | Messerli | |
| 6,991,653 B2 | 1/2006 | White | |
| 7,008,432 B2 | 3/2006 | Schläpfer | |
| 7,008,433 B2 | 3/2006 | Voellmicke | |
| 7,014,659 B2 | 3/2006 | Boyer, II | |
| 7,056,343 B2 | 6/2006 | Schäfer | |
| 7,060,073 B2 | 6/2006 | Frey | |
| 7,081,118 B2 | 7/2006 | Weber | |
| 7,118,580 B1 | 10/2006 | Beyersdorff | |
| 7,252,673 B2 | 8/2007 | Lim | |
| 7,294,134 B2 | 11/2007 | Weber | |
| 7,320,689 B2 | 1/2008 | Keller | |
| 7,387,635 B2 | 6/2008 | Keller | |
| 7,544,208 B1 | 6/2009 | Mueller | |
| 7,625,377 B2 | 12/2009 | Veldhuizen | |
| 7,641,693 B2 | 1/2010 | Gutlin | |
| 7,648,529 B2 | 1/2010 | An | |
| 7,691,147 B2 | 4/2010 | Gutlin | |
| 7,708,779 B2 | 5/2010 | Edie | |
| 7,749,231 B2 | 7/2010 | Bonvallet | |
| 7,806,899 B2 | 10/2010 | Hogg | |
| 7,819,922 B2 | 10/2010 | Sweeney | |
| 7,981,157 B2 | 7/2011 | Castleman | |
| 7,988,699 B2 | 8/2011 | Martz | |
| 8,241,294 B2 | 8/2012 | Sommerich | |
| 8,241,363 B2 | 8/2012 | Sommerich | |
| 2001/0007073 A1 | 7/2001 | Zucherman | |
| 2001/0012938 A1 | 8/2001 | Zucherman | |
| 2001/0016743 A1 | 8/2001 | Zucherman | |
| 2001/0016776 A1 | 8/2001 | Zuckerman | |
| 2001/0021850 A1 | 9/2001 | Zucherman | |
| 2001/0029377 A1 | 10/2001 | Aebi | |
| 2001/0031965 A1 | 10/2001 | Zucherman | |
| 2001/0031969 A1 | 10/2001 | Aebi | |
| 2001/0039452 A1 | 11/2001 | Zucherman | |
| 2001/0053602 A1 | 12/2001 | Lee | |
| 2002/0082695 A1 * | 6/2002 | Neumann | 623/17.11 |
| 2002/0107200 A1 | 8/2002 | Chang | |
| 2002/0123754 A1 | 9/2002 | Holmes | |
| 2002/0161441 A1 | 10/2002 | Lang | |
| 2002/0183746 A1 | 12/2002 | Zucherman | |
| 2003/0032964 A1 | 2/2003 | Watkins | |
| 2003/0065330 A1 | 4/2003 | Zucherman | |
| 2003/0149438 A1 | 8/2003 | Nichols | |
| 2003/0163199 A1 | 8/2003 | Boehm | |
| 2003/0171813 A1 * | 9/2003 | Kiester | 623/17.11 |
| 2003/0187453 A1 | 10/2003 | Schlapfer | |
| 2003/0191531 A1 | 10/2003 | Berry | |
| 2003/0199980 A1 | 10/2003 | Siedler | |
| 2003/0208272 A1 | 11/2003 | Crozet | |
| 2003/0220650 A1 | 11/2003 | Major | |
| 2003/0225414 A1 | 12/2003 | Shimp | |
| 2003/0225416 A1 | 12/2003 | Bonvallet | |
| 2003/0229355 A1 | 12/2003 | Keller | |
| 2004/0010261 A1 | 1/2004 | Hoag | |
| 2004/0039397 A1 | 2/2004 | Weber | |
| 2004/0049271 A1 | 3/2004 | Biedermann | |
| 2004/0059261 A1 | 3/2004 | Grinberg | |
| 2004/0098129 A1 | 5/2004 | Lin | |
| 2004/0106927 A1 | 6/2004 | Ruffner | |
| 2004/0172129 A1 | 9/2004 | Schafer | |
| 2004/0181283 A1 | 9/2004 | Boyer | |
| 2004/0186569 A1 | 9/2004 | Berry | |
| 2004/0199168 A1 | 10/2004 | Bertagnoli | |
| 2004/0220582 A1 | 11/2004 | Keller | |
| 2005/0015094 A1 | 1/2005 | Keller | |
| 2005/0015095 A1 | 1/2005 | Keller | |
| 2005/0021042 A1 | 1/2005 | Marnay | |
| 2005/0043804 A1 | 2/2005 | Gordon | |
| 2005/0055031 A1 | 3/2005 | Lim | |

(56) References Cited

U.S. PATENT DOCUMENTS

| | | |
|---|---|---|
| 2005/0080425 A1 | 4/2005 | Bhatnagar |
| 2005/0085910 A1 | 4/2005 | Sweeney |
| 2005/0090898 A1 | 4/2005 | Berry |
| 2005/0101960 A1 | 5/2005 | Fiere |
| 2005/0119665 A1 | 6/2005 | Keller |
| 2005/0143749 A1 | 6/2005 | Zalenski |
| 2005/0177173 A1 | 8/2005 | Aebi |
| 2005/0182416 A1 | 8/2005 | Lim |
| 2005/0187634 A1 | 8/2005 | Berry |
| 2005/0209697 A1 | 9/2005 | Paponneau |
| 2005/0216084 A1* | 9/2005 | Fleischmann et al. ..... 623/17.11 |
| 2005/0234550 A1 | 10/2005 | Metz-Stavenhagen |
| 2005/0261683 A1 | 11/2005 | Veldhuizen |
| 2006/0004377 A1 | 1/2006 | Keller |
| 2006/0025777 A1 | 2/2006 | Weber |
| 2006/0030856 A1 | 2/2006 | Drewry |
| 2006/0036258 A1 | 2/2006 | Zucherman |
| 2006/0058879 A1 | 3/2006 | Metz-Stavenhagen |
| 2006/0074431 A1 | 4/2006 | Sutton |
| 2006/0129241 A1 | 6/2006 | Boyer |
| 2006/0200244 A1 | 9/2006 | Assaker |
| 2006/0217712 A1 | 9/2006 | Mueller |
| 2007/0028710 A1 | 2/2007 | Kraus |
| 2007/0123987 A1 | 5/2007 | Bernstein |
| 2007/0161999 A1 | 7/2007 | Biedermann |
| 2007/0168040 A1 | 7/2007 | Raymond |
| 2007/0225409 A1 | 9/2007 | Matsumoto |
| 2007/0255408 A1 | 11/2007 | Castleman |
| 2007/0255410 A1 | 11/2007 | Dickson |
| 2007/0270964 A1 | 11/2007 | Strohkirch |
| 2008/0009864 A1* | 1/2008 | Forton et al. .................... 606/61 |
| 2008/0027544 A1* | 1/2008 | Melkent ..................... 623/17.11 |
| 2008/0039948 A1 | 2/2008 | Biedermann |
| 2008/0269901 A1 | 10/2008 | Baynham |
| 2009/0005874 A1 | 1/2009 | Fleischmann |
| 2009/0036985 A1 | 2/2009 | Whiting |
| 2009/0276050 A1 | 11/2009 | Biedermann |
| 2012/0277878 A1 | 11/2012 | Sommerich |

FOREIGN PATENT DOCUMENTS

| | | |
|---|---|---|
| EP | 968692 | 1/2000 |
| EP | 1090703 | 4/2001 |
| EP | 1188424 | 3/2002 |
| EP | 1491165 | 12/2004 |
| JP | 2000024946 | 1/2000 |
| WO | 9201428 | 7/1991 |
| WO | WO 9963913 | 12/1999 |
| WO | WO 02071986 | 9/2002 |
| WO | 2004089224 | 10/2004 |
| WO | 2006027098 | 3/2006 |

OTHER PUBLICATIONS

Kandziora, "Biomechanical Comparison of Expandable Cages for Vertebral Body Replacement in the Cervical Spine", *J Neurosurg*, Jul. 2003, vol. 99(1), pp. 91-97.

Thongtrangan, "Vertebral Body Replacement With an Expandable Cage for Reconstruction After Spinal Tumor Resection", *Neurosurg Focus*, Nov. 15, 2003, vol. 15(5) p. E8.

Coumans, "Use of the Telescopic Plate Spacer in Treatment of Cervical and Cervicothoracic Spine Tumors", *Neurosurgery*, Aug. 2002, vol. 51(2), pp. 417-426.

Pederson, "Thermal Assembly of a Biomimetic Mineral/Collagen Composite", Biomaterials. Nov. 2003; vol. 24(26), pp. 4881-4890.

Pflugmacher, "Biomechanical Comparison of Expandable Cages for Vertebral Body Replacement in the Thoracolumbar Spine", *Spine*, Jul. 1, 2004, vol. 29(13), pp. 1413-1419.

Woiciechowsky, "Distractable Vertebral Cages for Reconstruction After Cervical Corpectomy", *Spine*, Aug. 1, 2005, vol. 30(15), pp. 1736-1741.

Krbec, "Replacement of the Vertebral Body With an Expansion Implant", Acta Chir Orthop Traumataol Cech , 2002, pp. 158-162, vol. 69(3).

Krbec, "Percutaneous Anterior Odontoid Screw Fixation Technique. A New Instrument and a Cadaveric Study", Acta Neurochir Wien, 1999, pp. 521-524, vol. 141(5).

Khodadadyan-Klostermann, "Expandable Cages: Biomechanical Comparison of Different Cages for Ventral Spondylodesis in the Thoracolumbar Spine", CHIRUG, Jul. 2004, pp. 694-701, vol. 75(7).

PCT Search Report dated Jan. 23, 2012 for PCT/US2010/32491.

* cited by examiner

MINIMALLY INVASIVE CORPECTOMY CAGE AND INSTRUMENT

BACKGROUND OF THE INVENTION

A spinal corpectomy procedure seeks to remove a diseased vertebral body from the patient, and is commonly performed through an anterior approach using a large, open incision and general retractors. Increasingly, however, surgeons are utilizing smaller access portals for all types of surgeries, including spinal corpectomies. They also are more often using a posterior approach when the corpectomy involves the thoracic spine. However, this approach provides a more limited access to the spine, and often requires the surgeon to take a nerve root in order to use existing corpectomy cages and instruments. Surgeons who strive to keep their access windows small often resort to manipulating the corpectomy cage into position using sutures and small instruments, by first inserting the cage orthogonal to the axis of the spinal column, then and rotating it into place so that the endplates of the cage face the opposing vertebral bodies. A corpectomy implant and instrument designed for use through a small incision or port would make this cage placement easier and faster for the surgeon, and safer for the patient.

US Patent Publication No. 20080114467 (Capote) discloses an expandable medical implant for supporting bone structures. The implant may include an outer member and an inner member receivable in the outer member. One of the outer and inner members includes a tapered surface and the other of the outer and inner members includes a scalloped surface. The implant may also include a locking element disposed between the tapered surface and the scalloped surface. The tapered surface may be movable relative to the locking element to transversely shift the locking element into engagement with the scalloped surface to inhibit a decrease in the overall implant height.

US Patent Publication No. 20080167720 (Melkent) discloses an expandable vertebral replacement device and method of using the same that allows surgeons to support two adjacent vertebrae after an intermediate vertebra or a portion of an intermediate vertebra has been removed for the spine. The expandable vertebral replacement device includes a first replacement body, a second replacement body and a collar. The second replacement body includes a projecting portion that is telescopically received within an axial passage defined by the first replacement body. The collar is used to force the collet of the first replacement body into clamping engagement with the projecting portion of the second replacement body to lock the expandable vertebral replacement device at a select height.

PCT Patent Publication No. WO2006116052 (Rhoda) discloses an expandable prosthetic implant device for engagement between vertebrae generally comprising an inner member, outer member, and gear member positioned coaxial with respect to each other such that the inner and outer members are moveable relative to each other along an axis. The gear member is axially fixed to the outer member and freely rotatable with respect to the outer member and the gear member threadedly engages a threaded portion of the inner member to translate inner member along the axis. The implant is configured to engage the vertebrae in a predetermined alignment and the gear member includes gear teeth exposed to the exterior and configured to be accessible by a tool member at a plurality of angular positions around the perimeter of the implant device.

PCT Patent Publication No. WO2008065450 (Parry) discloses an implant for repairing a damaged body structure that comprises or is associated with bone parts. In one aspect a spinal implant includes an inferior member having an inferior end surface for engaging a superior face of an inferior vertebral body and a longitudinal portion; a superior member having a superior end surface for engaging an opposing inferior surface of a second vertebral body, and a portion adapted to cooperate with the longitudinal portion of the inferior member such that the superior member is moveable relative to the inferior member by sliding in the longitudinal direction; and fixating means for securing the superior member to the inferior member. Also described are instruments and methods used in the repair of such damaged body structures.

SUMMARY OF THE INVENTION

The present invention is directed to implants, instruments and methods of delivering a corpectomy implant into a spinal defect space and then rotating the corpectomy implant in the defect space without disconnecting it from its delivery instruments. In preferred embodiments, the instruments of the present invention are designed to work through a minimally invasive port. This minimally invasive approach thereby eliminates the need for the surgeon to take the local nerve root during the corpectomy procedure.

The present invention is further advantageous in that it also eliminates the need for a parallel expansion insertion device (which would require an open surgery), while maintaining a sufficient external expansion mechanism and a large graft volume inside the implant.

Preferred embodiments of the present invention feature an expandable corpectomy cage and an insertion instrument designed to both rotate and expand the cage.

In preferred embodiments, the expandable cage comprises an instrument attachment features, these feature including i) mating holes on the sides of the outer sleeve, and ii) a ball-shaped pocket on the endplate of the inner sleeve.

In preferred embodiments, the insertion instrument features:
 a) a tuning-fork shaped holder, which attaches to the mating holes on the implant's outer sleeve using small bosses which mate with the holes under the spring tension of the fork, and
 b) a lever with a spherical end that mates with the ball-shaped pocket in the inner sleeve endplate.

In other embodiments, the mating provided by the spring tension of the fork can be accomplished with a pivot and lock.

Therefore, in accordance with the present invention, there is provided a spacer for insertion between two vertebrae, the spacer having a variable axial height and comprising:
 a) an outer member comprising an inner wall and an outer wall having a pair of attachment features thereon adapted for mating with an insertion instrument,
 b) an inner member comprising an outer wall and an end plate having a pocket having a substantially curved bottom thereon adapted for mating with the instrument,
wherein the outer wall of the inner member is received within the inner wall of the outer member and is axially adjustable relative thereto in an axial direction thereof for adjusting the variable axial height of the spacer.

Also in accordance with the present invention, there is provided a spacer for insertion between two vertebrae by an insertion instrument, the spacer having a variable axial height and comprising:

a) an outer member comprising an inner wall and an outer wall having a pocket having a substantially curved bottom thereon adapted for mating with a first portion of the instrument,
b) an inner member comprising an outer wall and an end plate having a pair of attachment features thereon adapted for mating with a second portion of the instrument, wherein the outer wall of the inner member is received within the inner wall of the outer member and is axially adjustable relative thereto in an axial direction thereof for adjusting the variable axial height of the spacer.

Also in accordance with the present invention, there is provided an assembly for inserting a spacer between two vertebrae, the assembly comprising:
i) the spacer having a variable axial height and comprising:
a) an outer member comprises an inner wall and an outer wall having a pair of attachment features thereon adapted for mating with an instrument,
b) an inner member comprises an outer wall and an end plate having a pocket having a substantially curved bottom thereon adapted for mating with the instrument,
wherein the outer wall of the inner member is guided within the inner wall of the outer member to be adjustable relative thereto in an axial direction thereof for adjusting an overall height, and
ii) an insertion instrument comprising:
a) a fork comprising a proximal shaft comprising a handle, an intermediate crossbar, and a distal portion comprising a pair of extensions, the extensions having a pair of opposing bosses,
b) a lever having a proximal shaft comprising a handle, an intermediate portion and a substantially curved distal end,
wherein the intermediate portion of the lever pivots upon the crossbar,
wherein the opposing bosses mate with the pair of attachment features, and
wherein the substantially curved distal end of the lever pivotally mates with the substantially curved bottom of the pocket.

Also in accordance with the present invention, there is provided a method of inserting an expandable spinal corpectomy cage into a defect space between a pair of vertebral bodies, the cage comprising i) an outer member having a first endplate and opposing attachment features defining a rotation axis, and ii) an inner member having a second endplate, wherein the inner member is received within the outer member and is axially adjustable relative thereto in an axial direction thereof for adjusting the variable axial height of the cage, the method comprising the steps of:
a) attaching the attachment features of the expandable cage to an insertion instrument,
b) inserting the expandable cage into the defect space in an orientation in which the axis of the cage is substantially orthogonal to an axis of the spine, and
c) manipulating the insertion instrument to rotate the expandable cage about the rotation axis so that the axis of the cage is substantially parallel to the axis of the spine.

DETAILED DESCRIPTION OF THE INVENTION

Figure 1:
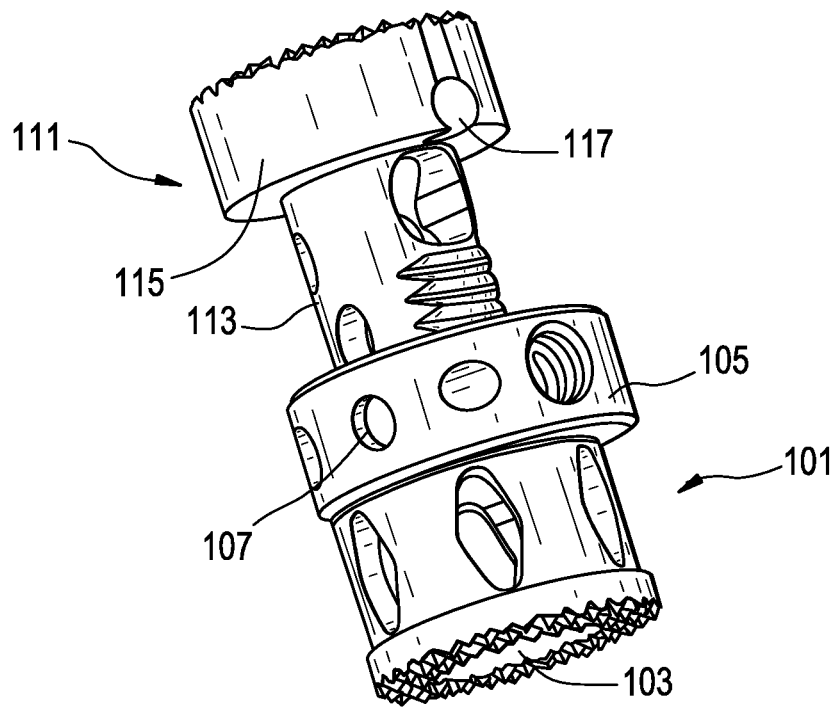
FIG. 1 discloses an expandable cage of the present invention comprising instrument attachment features, including mating holes on the sides of the outer sleeve, and a ball-shaped pocket on the endplate of the inner sleeve.

Now referring to FIG. 1, there is provided a spacer 150 for insertion between two vertebrae, the spacer having a variable axial height and comprising:
a) an outer member 101 comprising an inner wall 103 and an outer wall 105 having a pair of recesses 107 thereon adapted for mating with an instrument,
b) an inner member 111 comprising an outer wall 113 and an end plate 115 having a substantially spherical pocket 117 thereon adapted for mating with the instrument,
wherein the outer wall of the inner member is received within the inner wall of the outer member and is axially adjustable relative thereto in an axial direction thereof for adjusting the variable axial height of the spacer.

Figure 2:
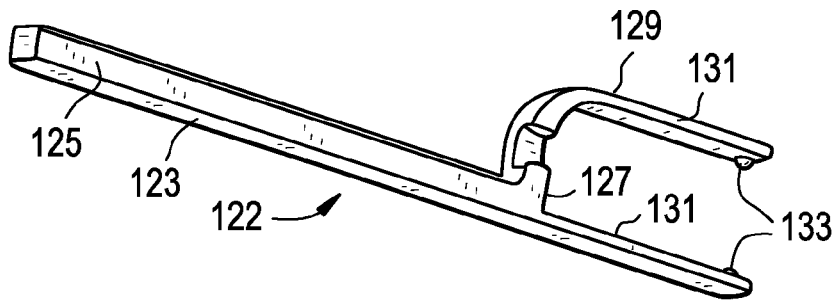
FIG. 2 discloses a first instrument component of the present invention, namely, a tuning-fork shaped holder, which attaches to the mating holes on the implant's outer sleeve using small bosses which mate with the holes under the spring tension of the fork.

Now referring to FIG. 2, there is provided a first component of the delivery instrument, comprising a fork 122 comprising a proximal shaft 123 comprising a handle 125, an intermediate crossbar 127 (fulcrum), and a distal portion 129 comprising a pair of extensions 131, each extension having a pair of opposing bosses 133.

Figure 3:
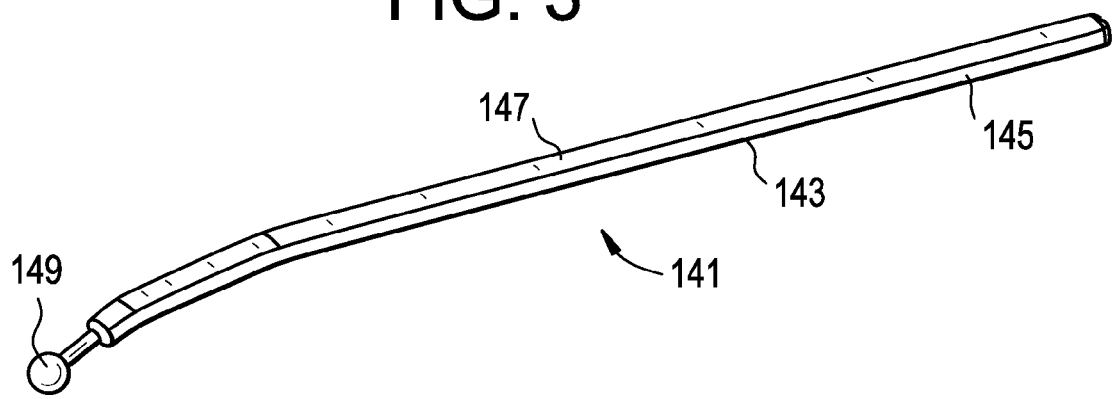
FIG. 3 discloses a second instrument component of the present invention, namely, a lever with a spherical end that mates with the ball-shaped pocket in the inner sleeve endplate.

Now referring to FIG. 3, there is provided a second component of the delivery instrument, comprising a lever 141 having a proximal shaft 143 comprising a handle 145, an intermediate portion 147 and a substantially spherical distal end 149.

In preferred embodiments, the cage of the present invention is inserted into the defect space in the following manner:

First, the surgeon accesses the spinal level of interest by removing the target vertebral body through a small incision or portal.

Figure 4A:
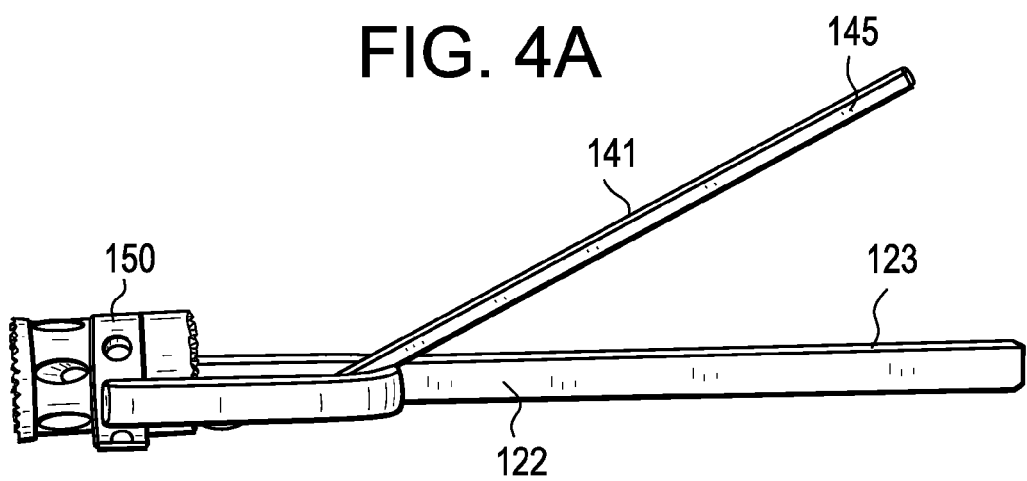
FIG. 4a discloses the cage of the present invention attached to the instrument of the present invention.

Next, and now referring to FIG. 4a, an appropriately-sized cage 150 is selected and attached to the fork 122 by snapping the fork's bosses 133 over the recesses 7 on the outer member of the cage. Next, the lever 141 is attached to the inner sleeve pocket 117 by sliding its spherical end 149 into the pocket from under the inferior side of the superior endplate. Next, the cage is collapsed, and the handles of the fork 125 and lever 145 are oriented to be parallel to the main axis of the cage.

Figure 4B:
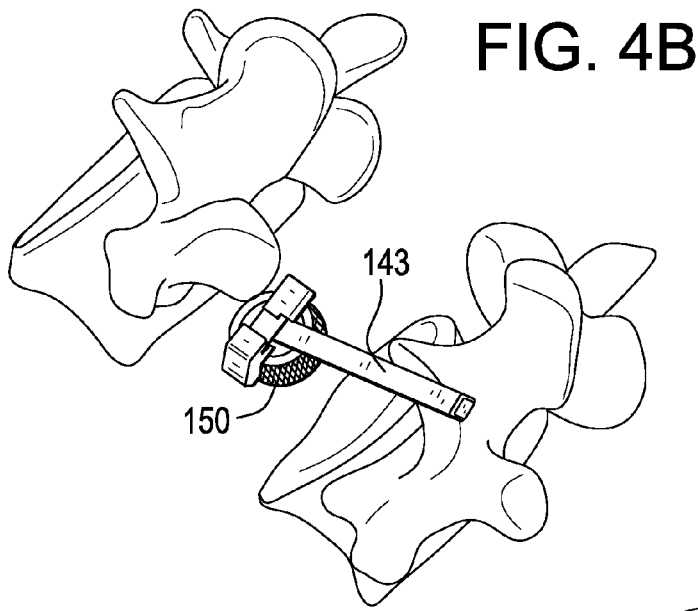
FIGS. 4b and 4c disclose insertion of the cage into a defect space in a minimally invasive orientation.
Figure 4C:
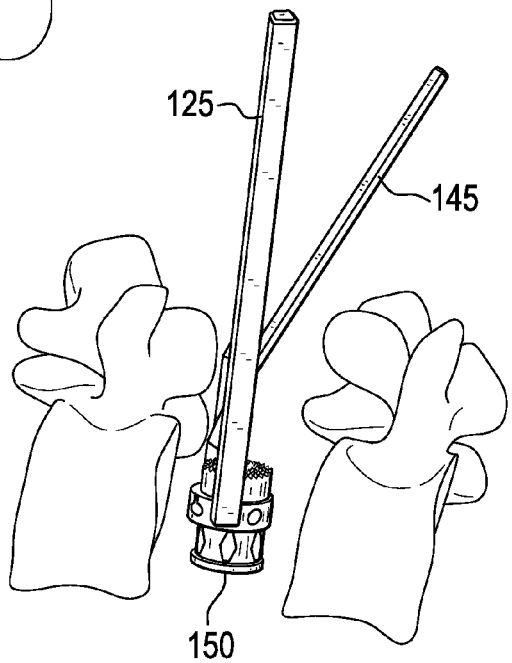

Next, and now referring to FIGS. 4b and 4c, the surgeon holds the handles 125,145 together, and inserts the cage 150 through an access portal (not shown).

Figure 4D:
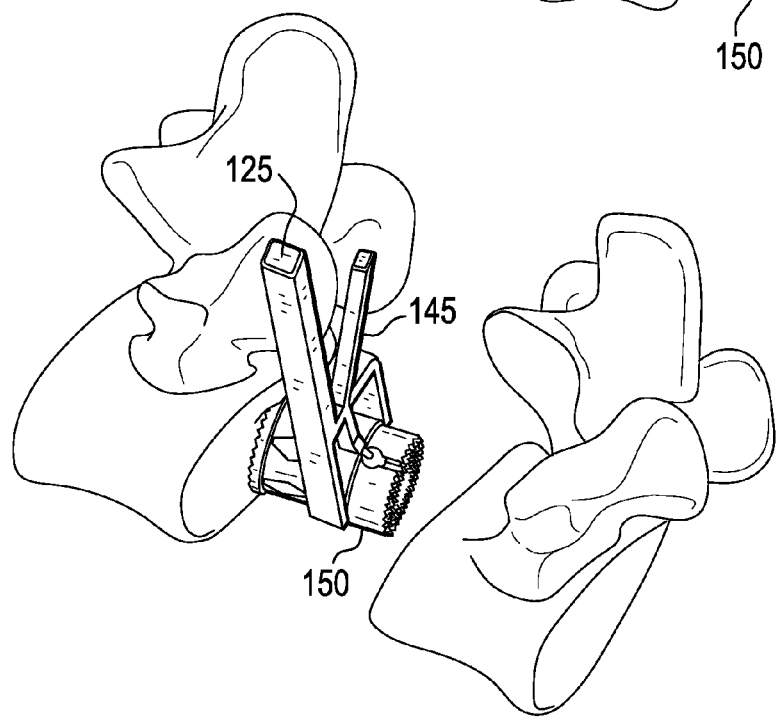
FIG. 4d discloses rotating the cage 90 ninety degrees.

Now referring to FIG. 4d, once the cage 150 is in the defect at the desired location (but not orientation), the surgeon manipulates the two handles 125,145 to flip the cage ninety degrees, thereby making it parallel to the axis of the spine.

Figure 4E:
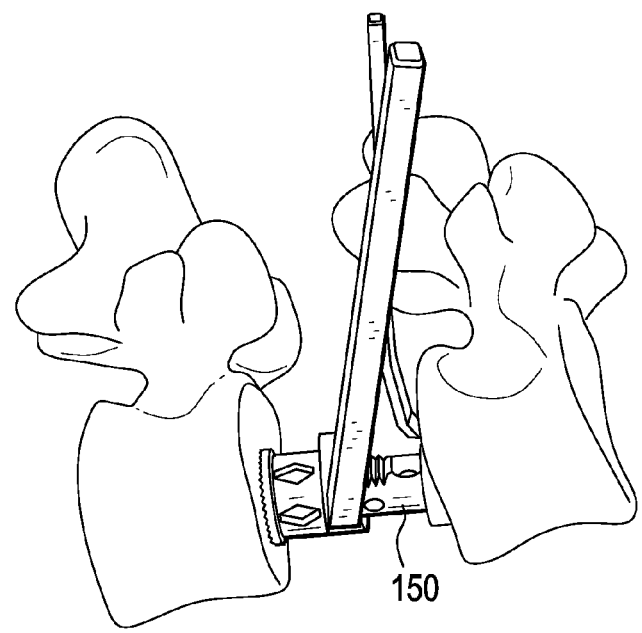
FIG. 4e discloses expansion of the rotated cage.

Now referring to FIG. 4e, expansion of the cage 150 is then initiated by placing the intermediate portion 147 of the lever against the horizontal crossbar 127 of the fork, and squeezing the handles together.

Figure 4F:
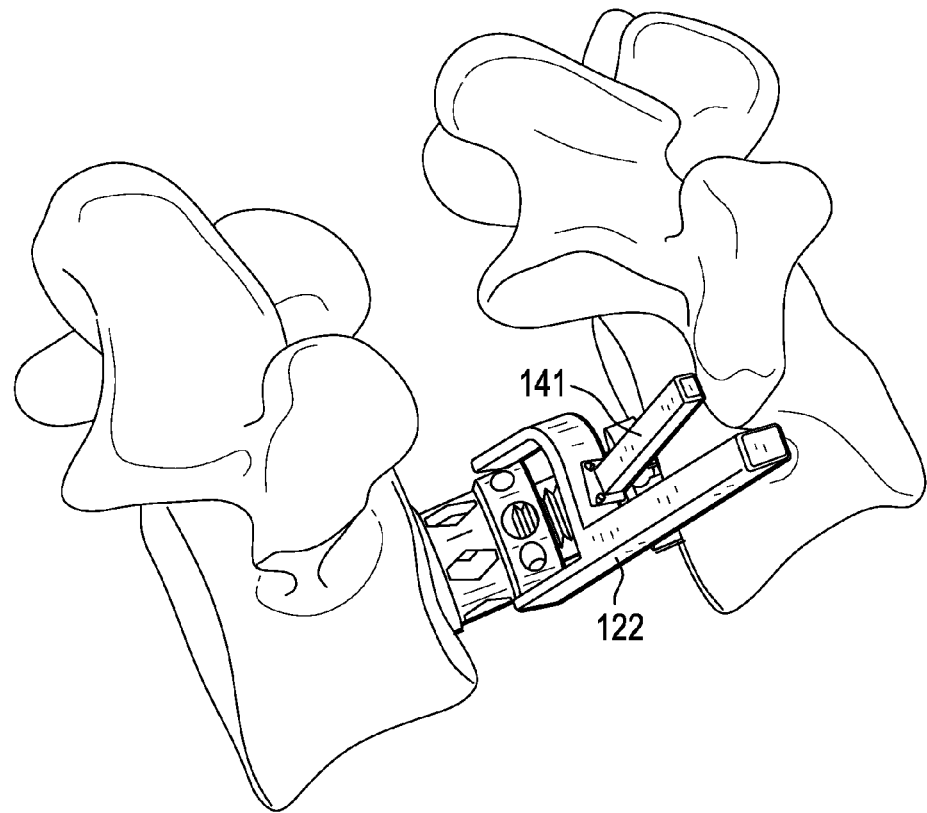
FIG. 4f discloses rotation of the instrument to allow access to the set screw.

Now referring to FIG. 4f, the fork 122 and lever 141 can be rotated slightly while still under tension, allowing access to a set screw on the cage with a straight, thin driver. Once the set screw is locked, the fork is removed by pulling it straight up to overcome the spring tension in the fork. The lever is removed by sliding it out from under the superior endplate.

Figure 5A:
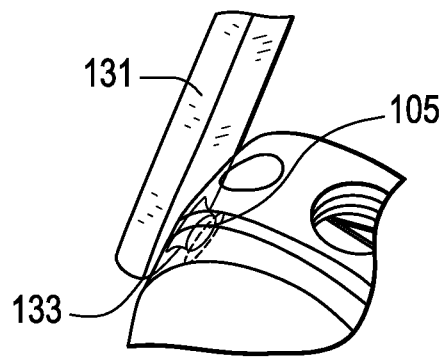
FIGS. 5a-5j disclose a series of steps performed by the surgeon in order to insert and expand the cage of the present invention.

A more detailed presentation of the procedure for inserting the present invention is provided in FIGS. 5a-5j and is presented below:

Now referring to FIG. 5a, the fork extensions 131 are attached to the implant, with the extension bosses 133 resting in the recesses 107 on the wall 105 of the outer member of the implant. This attachment configuration allows rotation of the implant about the bosses. The spring-loaded nature of the extensions of the fork allow them to snap over the implant body.

Figure 5B:
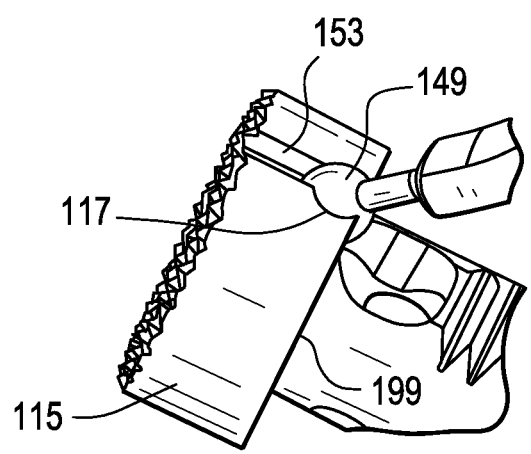
Figure 5C:
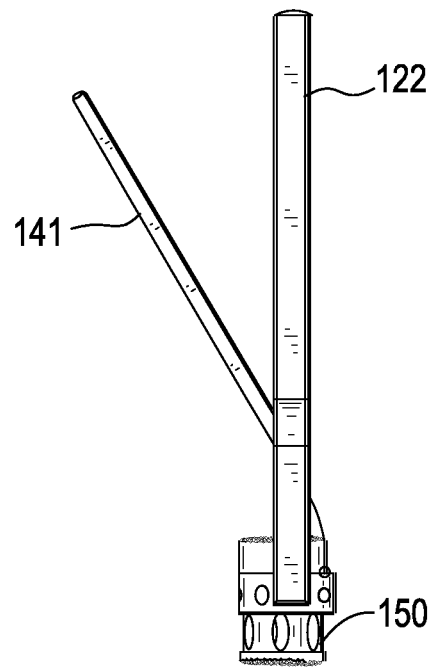

Now referring to FIG. 5b, the spherical distal end 149 of the lever is mounted in the spherical pocket 117 located on the implant. This spherical distal end is mounted in the pocket through an underside 199 of the endplate portion 115 of the inner member. Slot 153 provided above the spherical pocket on the endplate allows the lever to rotate into an insertion position Now referring to FIG. 5c, the fork 122 and the lever 141 are held together in-line with the longitudinal axis of the implant as the implant 150 is inserted between the vertebrae.

Figure 5D:
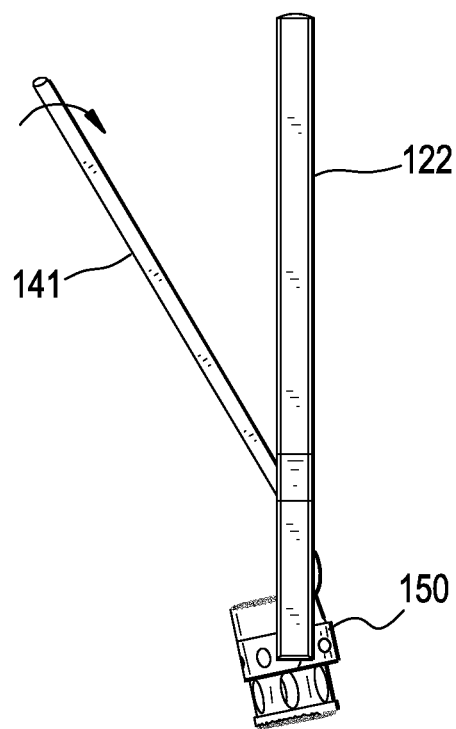

Now referring to FIG. 5d, the fork 122 is held steady while the lever 141 is manipulated to begin rotation of the implant 150.

Figure 5E:
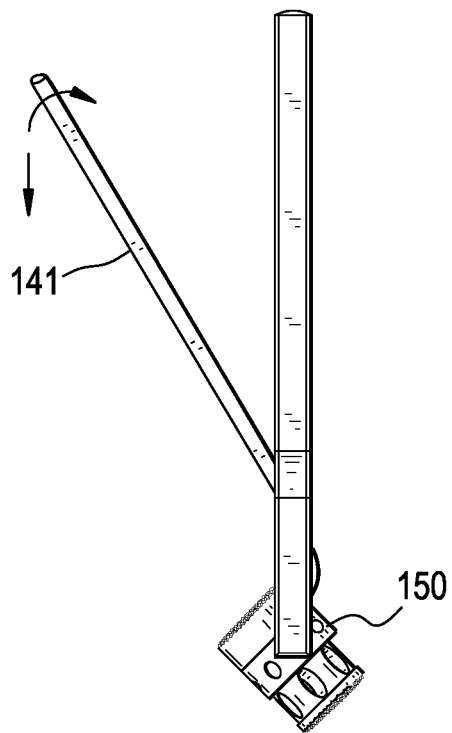

Now referring to FIG. 5e, rotation of the implant 150 about the bosses 133 continues by continued manipulation of the lever 141.

Figure 5F:
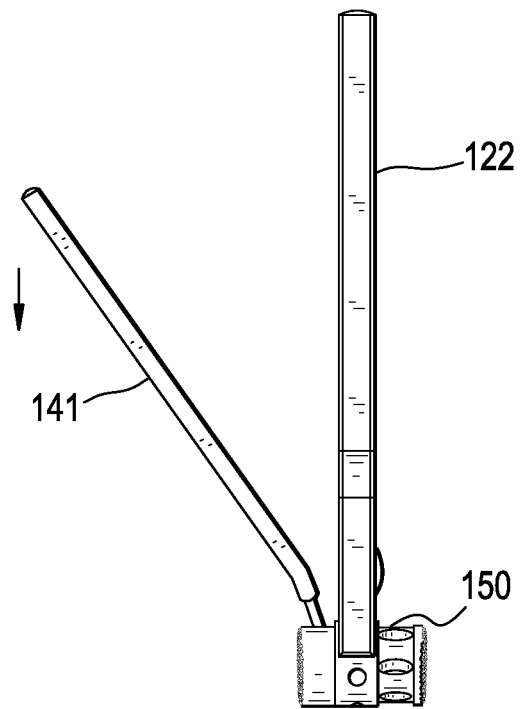

Now referring to FIG. 5f, rotation of the implant 150 to its final orientation is accomplished by pushing the lever 141 down while holding onto the fork 122.

Figure 5G:
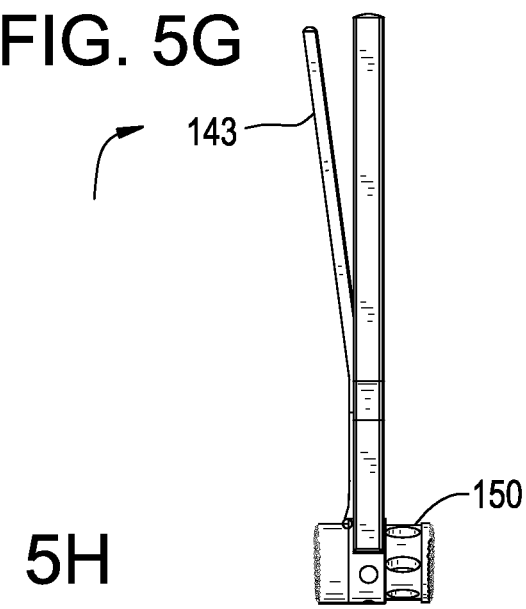

Now referring to FIG. 5g, once the implant 150 has been rotated to its final orientation and the implant endplates seat against the endplates of the vertebral bodies, the proximal shaft 143 of the lever is swung upwards to more substantially align with the proximal shaft 123 of the fork.

Figure 5H:
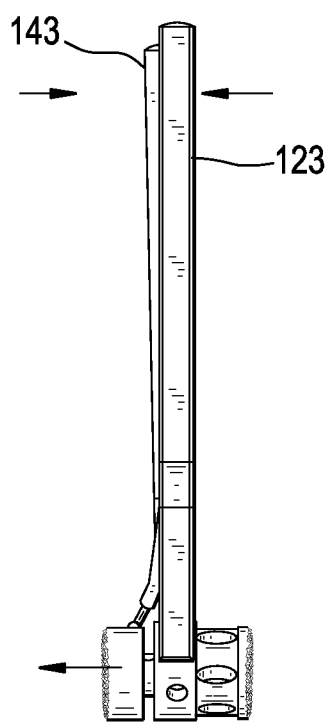
Figure 5I:
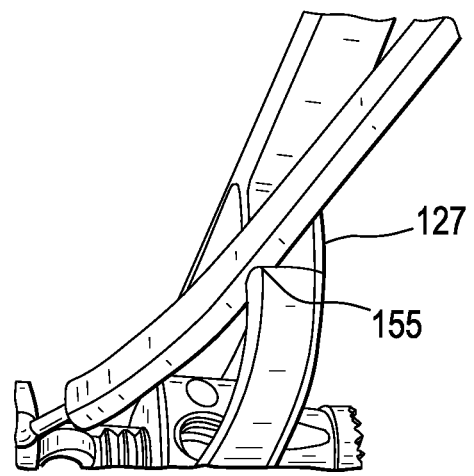

Now referring to FIGS. 5h and 5i, to begin expansion of the implant, the shafts 143,123 of the lever and fork are squeezed together. In this configuration, the lever mates with a slot 155 on the cross-bar of the fork so that the crossbar 127 behaves as a fulcrum in order to expand the implant.

Figure 5J:
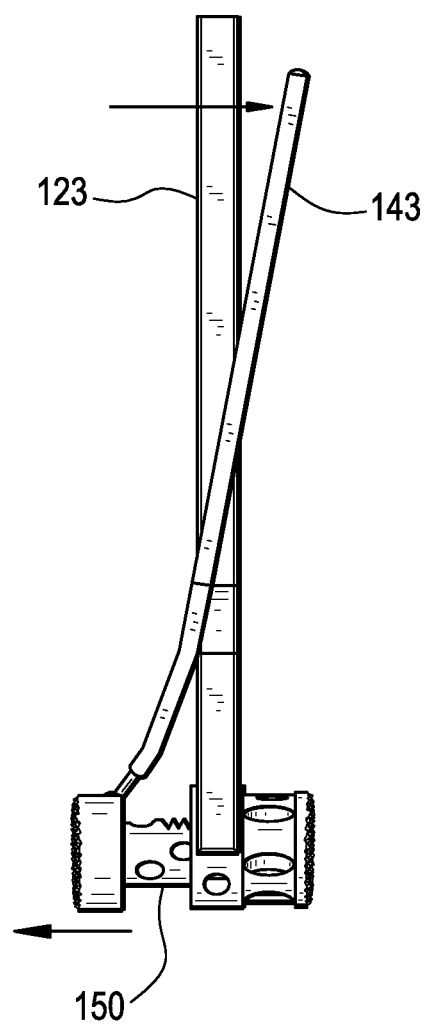

Now referring to FIG. 5j, to complete expansion of the implant 150, the shaft 143 of the lever is typically pushed past the shaft 123 of the fork, depending upon the amount of expansion needed.

Generally, the attachment features of the cage can be any conventional feature that is used to attach an implant to an insertion instrument. Preferably, the attachment feature is a recess having a shape corresponding to the bosses of the insertion instrument. Also preferably, the cage has a pair of attachment features that are located on diametrically opposite sides of a cage wall. Although the attachment features are shown in the FIGS. as recesses, in other embodiments, the attachment features can also be projections (in which case, the insertion instrument possesses corresponding recesses).

Generally, the pocket has a curved bottom that facilitates the pivoting of the cage. Preferably, the curved surface has a circular cross section in the axial direction. More preferably, the pocket has a substantially spherical shape. In other embodiments, the pocket has a cylindrical shape. In general, the distal end of the lever component possesses a feature that matingly corresponds to the pocket shape on the cage. For example, when the cage's pocket is substantially spherical, the lever's distal end is likewise substantially spherical.

Figure 6A:
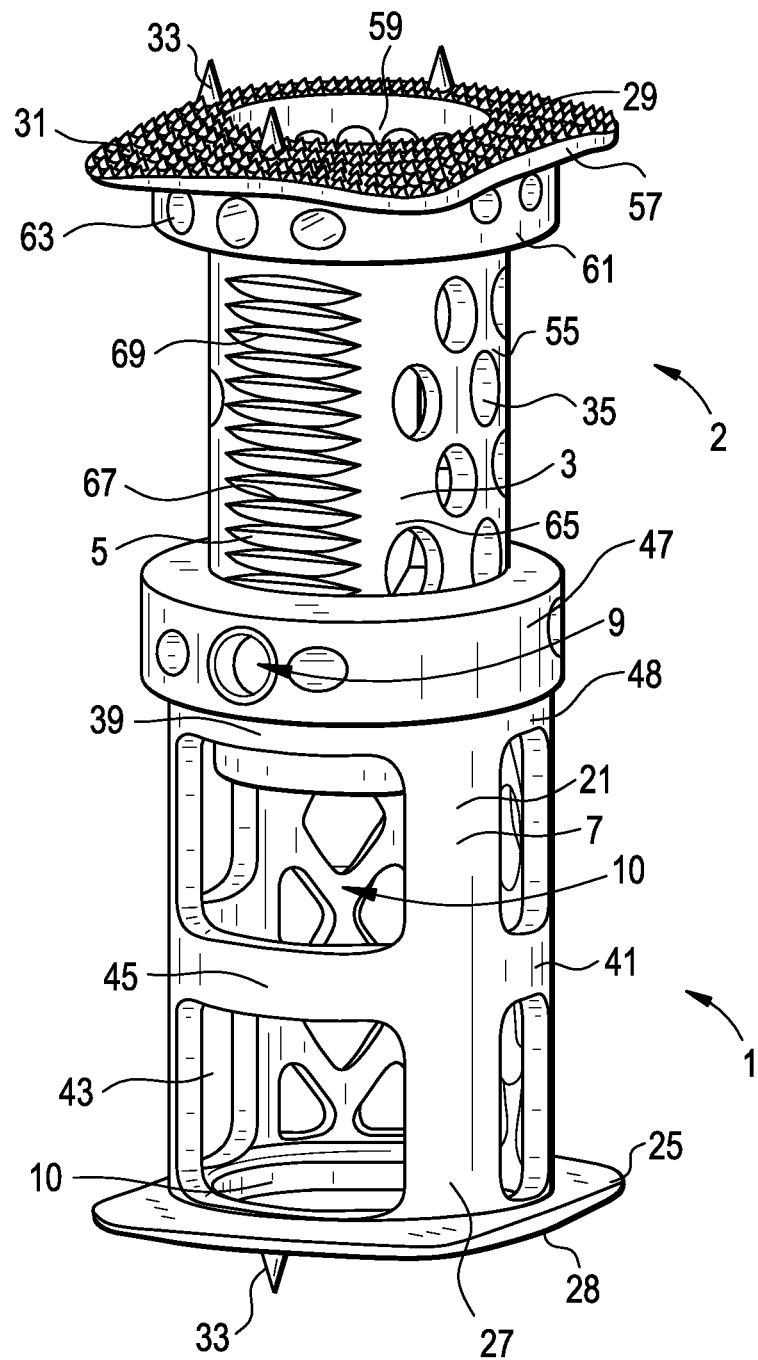
FIGS. 6a and 6b disclose front and back views of a cage of the present invention.
Figure 6B:
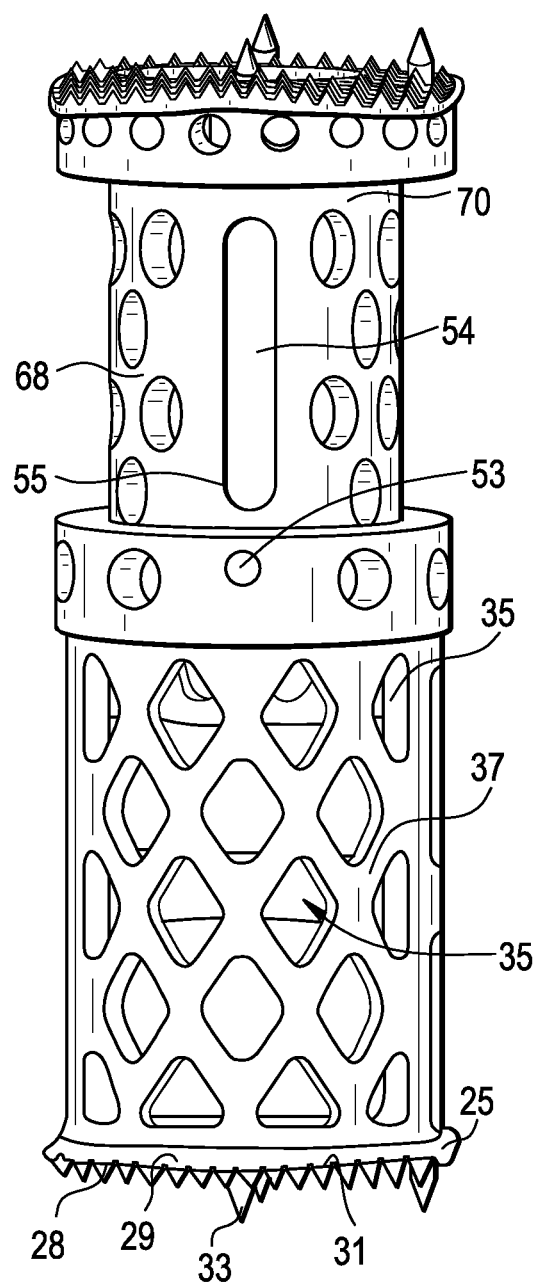
Figure 6C:
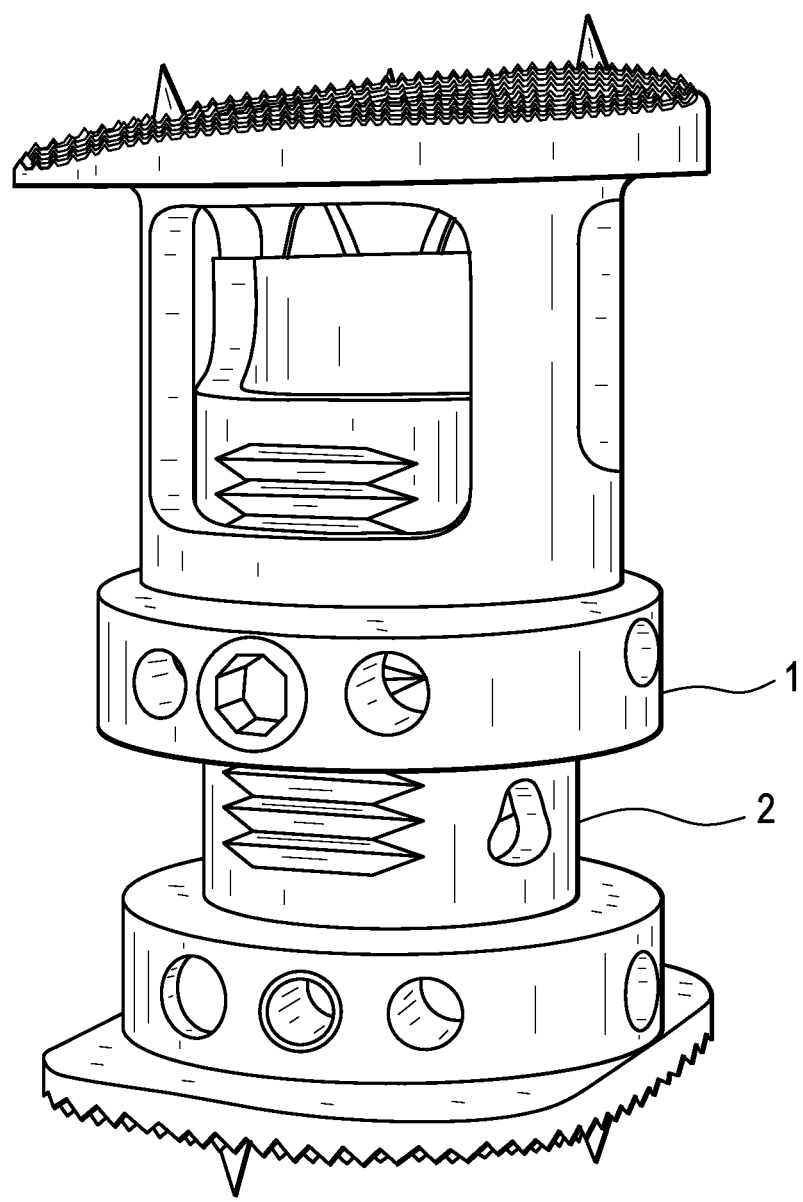
FIG. 6c discloses a cage of the present invention having windows in both annuluses.

Now referring to FIGS. 6a-6c there is provided a spacer for insertion between two vertebrae, the spacer having a variable axial height and comprising a sleeve-shaped first member 1 and a second member 2 guided within the first member to be slidable relative thereto in an axial direction thereof for adjusting an overall height, wherein the second member comprises an outer wall 3 and ratchet notches 5 provided at its outer wall facing the first member and extending in the axial direction, and wherein the first member comprises a wall 7 having an engagement member 9, which cooperates with the ratchet notches for adjusting the overall height of the spacer, wherein the first member has a window 10 therein for inserting graft material therethrough, and wherein the engagement member 9 comprises i) a set screw 11 and ii) a pressure plate 13 having an outer face 15 contacting the set screw and an inner face 17 having teeth 19 adapted to mate with the ratchet notches of the second member.

The first member generally has a tubular shape comprising a first annulus 21. The outer end of the first member should be adapted to seat upon a lower vertebral endplate, and so a substantially flat endplate 25 is generally attached to the outer end 27 of the first annulus. This endplate generally has a hole in its center and extends outwardly substantially radially from the outer end of the annulus. The outer face 28 of the endplate should be adapted to grip the lower vertebral endplate and so is generally provided with roughened features 29. These roughened features may be a plurality of uniformly distributed, pointed teeth 31 that bite into the adjacent endplate. In other embodiments, the teeth may be non-uniformly distributed. For further insuring that the endplate will be stably seated into the vertebral endplate, the outer face of the endplate may also have a few long spikes 33 extending therefrom. In some embodiments, the endplate has an overall convex shape in order to suitably conform to the overall concave shape of the natural vertebral endplate in which it seats. In some embodiments (as in FIG. 6), the endplate has a wedge cross-section in order to conform to the lordosis adopted by the natural spine in the region of the implant. Typically, the wedge is designed to provided a lordotic angle of between about 0 and about 24 degrees, more typically between about 6 and about 12 degrees. The wedge may also be designed to provided a kyphotic angle of between about 0 and about −12 degrees, In general, the outer dimensions of the endplates of the present invention are between about 16 mm and about 30 mm (e.g., 16×20; 20×23 and 24×30).

The annular portion of the first member also comprises a plurality of uniformly distributed, transverse, through-holes 35. These throughholes are generally about 2-8 mm in diameter, and provide a means for bone growth therethrough. The holes are preferably of diamond shape, although other shapes such as triangles may be used. When in a diamond shape, suitable sizes include 2.5 mm×3.5 mm shapes to 5 mm×7 mm shapes. In the particular FIGS. 6a and 6b, the throughholes have a diamond shape. The diamond shape allows the annulus material to make a mesh pattern in the wall that has structural advantages. However, any conventional shape may be used for the through-hole pattern. In some embodiments, the plurality of throughholes occupy only the distal portion 37 of the annulus. In such an embodiment, graft windows may be placed both on the proximal 39 and lateral 41 portions of the annulus. This has the advantage of allowing the surgeon to place bone graft into the cage from a variety of angles. In some embodiments, the plurality of throughholes occupy not only the distal portion of the first annulus, but also the lateral portions as well. In such an embodiment, graft windows may be placed only through the proximal portion of the annulus, but the cage has the structural advantage of extra strength.

The first member generally has at least one graft window 10 therein. The graft window functions both as a path through which the surgeon can place bone graft into the cage, but also as a means for bone growth therethrough. In other embodiments, the first member has a plurality of graft windows therein. When a face of the annulus has been selected for graft windows, in preferred embodiments, two graft windows 43 are placed one on top of the other, being separated by a bar 45. This bar enhances the strength of the cage. In the particular cage shown in FIG. 6, there are two graft windows on the proximal face of the annulus, two graft windows on the left lateral face of the annulus and two graft windows on the right lateral face of the annulus. This configuration represents a balance between providing surgeon flexibility (through the inclusion of multiple faces with graft windows) and cage strength (through the use of a lateral bar between windows on any face). Each window typically has a diameter of between about 5 mm and about 20 mm. Typical windows measure 5.5 mm×5.6 mm to 12 mm×15.75 mm to 17.5 mm×12 mm.

The first member may preferably include a reinforcing collar 47 surrounding the inner (upper) end portion 48 of the first annulus. The function of the reinforcing collar is to strengthen the first member and reduce deflection when the screw is tightened. The reinforcing collar also generally has a threaded screw hole extending radially therethrough. This threaded screw hole is adapted for threadable passage of a threaded locking set screw therethrough.

Figure 7A:
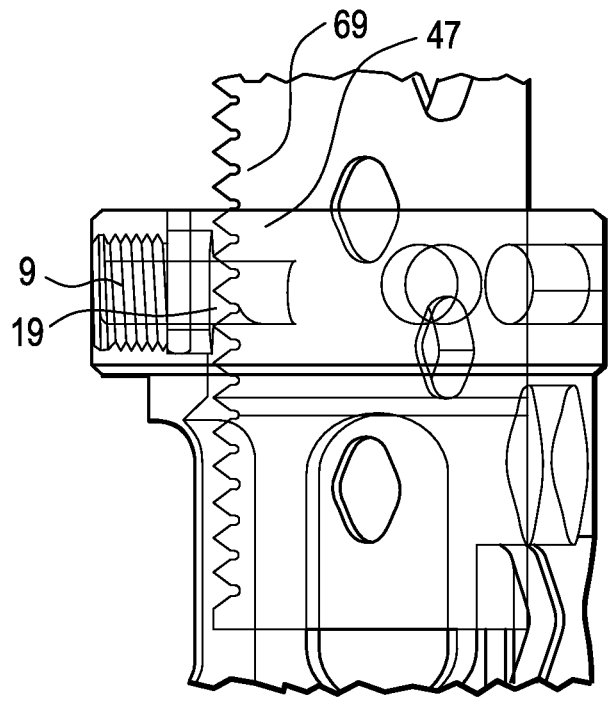
FIG. 7a discloses a cage of the present invention in which the teeth of the pressure plate mate with the notches on the inner annulus.

Now referring to FIG. 7a, the first member comprises a collar 47 having an engagement member 9 therein, and the engagement member cooperates with the ratchet notches of the second member for adjusting a desired overall height of the spacer.

Figure 7B:
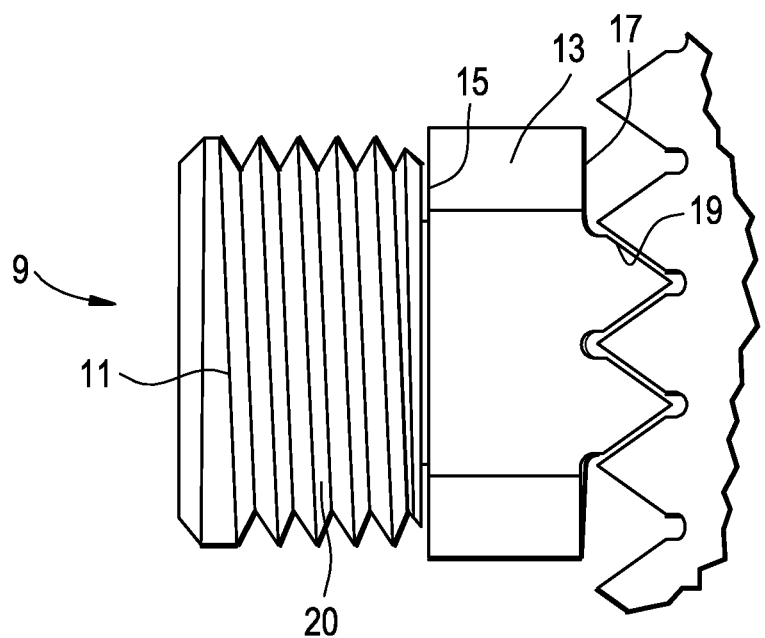
FIG. 7b discloses details of the engagement mechanism of the present invention.

Now referring to FIG. 7b, there is provided a more detailed understanding of the engagement member. The engagement member 9 comprises i) a set screw 11 and ii) a pressure plate 13 having an outer face 15 contacting the set screw and an inner face 17 having teeth 19 adapted to mate with the ratchet notches of the second member.

In some embodiments, as in FIG. 7b, a cylindrical outer surface 20 of the set screw is threaded to allow its advance toward the second member. In some embodiments, as in FIGS. 8a and 8b, the set screw is tubular with internal axial recesses 22 therein extending along its axis. These axial recesses mate with a screwdriver, thus allowing the screw to be rotated and thereby advanced towards the second member.

The set screw further has a neck and head extension 49 extending from its distal end 50, wherein the extension is shaped so as to both provide engagement with a corresponding recess 51 of the pressure plate and allow its rotation during that engagement.

Figure 8A:
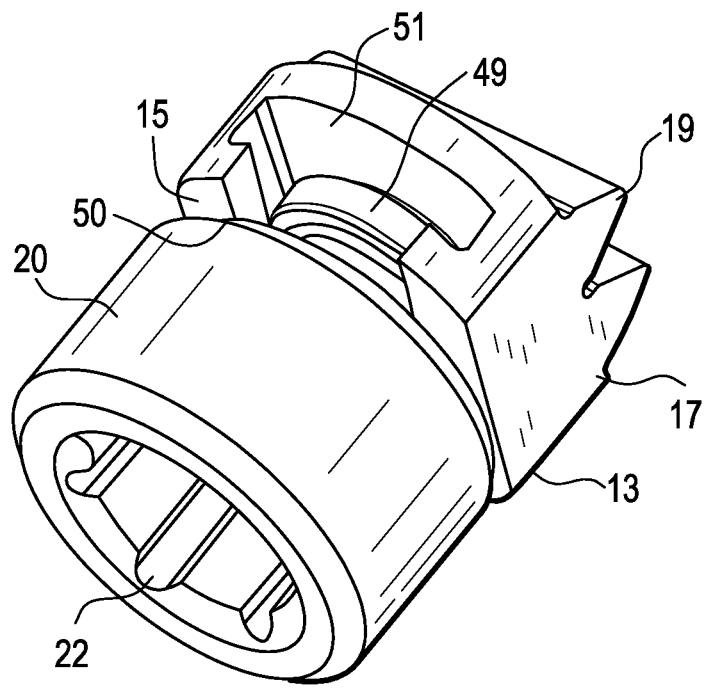
FIG. 8a discloses a perspective view of the engagement member of the present invention.
Figure 8B:
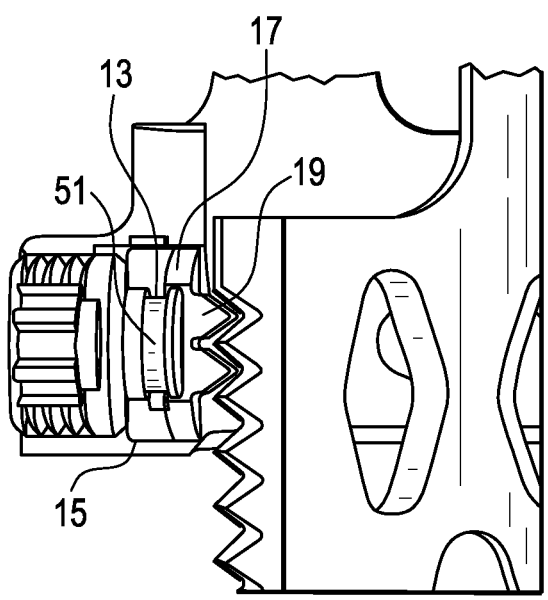
FIG. 8b discloses a cross-section of the engagement mechanism of the present invention having a pressure plate.

Now referring to FIGS. 8a and 8b, the pressure plate 13 has an outer face 15 contacting the set screw and an inner face 17 having teeth 19 adapted to mate with the ratchet notches of the second member. The outer face has a neck and head recess 51 therein that corresponds with the head and neck extension of the set screw so as to both provide engagement with a corresponding extension of the set screw and allow rotation of the set screw during that engagement. The pressure plate is seated on the inside face of the collar.

The inner face of the pressure plate has at least two elongated teeth 19 thereon forming at least one notch therebetween. The tips of the teeth are preferably spaced apart a distance of between about 1 mm and 2 mm, generally about 1.5 mm. The spacing can be larger or smaller than these values, with smaller being preferable.

Now referring to FIG. 6b, the distal 37 portion of the first member also has an assembly pin 53 extending radially inward from the collar. This assembly pin slidably mates with a corresponding assembly groove 54 of the second member in order to maintain the second member in a slidable orientation within the first member, and to retain the first member to the second member.

Still referring to FIG. 6b, the second member generally has a tubular shape comprising a second annulus 55. The outer diameter of the second annulus should be slightly smaller than the inner diameter of the first annulus of the first member, in order to provide slidable reception of the second annulus within the first member.

The outer end of the second member should be adapted to seat upon an upper vertebral endplate, and so a substantially flat endplate 57 is generally attached to the outer end 59 of the second annulus 55. This endplate generally has a hole in its center and extends outward substantially radially from the upper end of the annulus. The outer face of the endplate should be adapted to grip the upper vertebral endplate and so is generally provided with roughened features 29. These roughened features may be a plurality of uniformly (or non-uniformly) distributed, pointed teeth 31 that bite into the adjacent endplate. For further insuring that the endplate will be stably seated into the vertebral endplate, the outer face of the endplate may also have a few long spikes 33 extending therefrom. In some embodiments, the endplate has an overall convex shape in order to suitably conform to the overall concave shape of the natural vertebral endplate in which it seats.

The annular portion of the second member also comprises a plurality of uniformly distributed, transverse, through-holes 35. These throughholes are generally of the throughhole size discussed above, and provide a means for bone growth therethrough. In this particular FIG. 6a, the throughholes have a diamond shape. The diamond shape allows the second annulus material to make a mesh pattern that has structural advantages. However, any conventional shape may be used for the through-hole pattern. In some embodiments, the plurality of throughholes occupy each of the lateral faces of the posterior portion of the second annulus.

The second member may preferably include a reinforcing collar 61 surrounding the outer (upper) end portion 59 of the second annulus. The function of this reinforcing collar is to allow for instrument attachment. The reinforcing collar also generally has a plurality of through-holes 63 extending radially therethrough. These throughholes function as areas for instrument attachment, and as areas for bone growth and vascularization.

The proximal portion 65 of the second annulus has a plurality of elongated teeth 67 thereon forming at least one notch 69 therebetween. These teeth and notches form a row extending up the outside of the annulus. Typically, the annulus of the second member has at least ten elongated notches thereon. These notches are formed to compliment the teeth of the pressure plate. The apices of the notches on the second member are generally spaced apart a distance of between about 1 mm and 2 mm, generally about 1.5 mm. The spacing can be larger or smaller than these values, with smaller being preferable.

The distal 70 portion of the second annulus of the second member also has an assembly groove 54 extending inwardly and axially along the outside 68 of the second annulus. This assembly groove mates with the corresponding assembly pin of the first member in order to maintain the second member in a slidable orientation within the first member.

Once the overall height of the cage has been determined by the surgeon and the relative disposition of the first and second members set accordingly, the set screw is then rotated by the surgeon using a screwdriver. The set screw acts to advance the pressure plate so that the teeth on the pressure plate contact the ratchet notches of the second member, thereby locking the desired overall height of the cage.

Typically, the cages of the present invention are designed to occupy either one, two or three levels of a thoracolumbar corpectomy. In some embodiments having either 16 mm or 20 mm endplate dimensions, the height of the cage can be between 22 mm and 72 mm. In some embodiments having 24 mm endplate dimensions, the height of the cage can be between 22 mm and 110 mm. In general, the cage is designed to expand its height in an increment of between about 8.5 mm to about 25 mm. Cages can be designed to overlap in height ranges with their adjacent sizes. For example a first cage can range in height from 25 to 33.5 mm, while a second cage can range in height from 28.5 mm to 38.5 mm in height.

I claim:

1. An assembly for inserting a spacer between two vertebrae, the assembly comprising:
    i) a spacer having a variable axial height and comprising:
        a) an outer member comprising an inner wall and an outer wall having a pair of attachment features thereon adapted for mating with an instrument,
        b) an inner member comprising an outer wall and an end plate having a pocket having a substantially curved bottom thereon adapted for mating with the instrument,
    wherein the outer wall of the inner member is guided within the inner wall of the outer member to be adjustable relative thereto in an axial direction thereof for adjusting an overall height, and
    ii) an insertion instrument comprising:
        a) a fork comprising a proximal shaft comprising a handle, an intermediate crossbar, and a distal portion comprising a pair of extensions, the extensions having a pair of opposing bosses,
        b) a lever having a proximal shaft comprising a handle, an intermediate portion and a substantially curved distal end,
    wherein the intermediate portion of the lever pivots upon the crossbar,
    wherein the opposing bosses mate with the pair of attachment features, and
    wherein the substantially curved distal end of the lever pivotally mates with the substantially curved bottom of the pocket.

2. The assembly of claim 1 wherein the attachment features are selected from the group consisting of a recess and a projection.

3. The assembly of claim 1 wherein the pocket has a substantially spherical portion.

* * * * *